(12) United States Patent
Roberts (10) Patent No.: US 6,360,119 B1
(45) Date of Patent: Mar. 19, 2002

(54) ELECTRODE PLACEMENT DEVICE FOR TAKING ELECTROCARDIOGRAMS AND METHOD OF USE

(76) Inventor: Lauri E. Roberts, 2119 Caves Rd., Owings Mills, MD (US) 21117

( * ) Notice: Subject to any disclaimer, the term of this patent is extended or adjusted under 35 U.S.C. 154(b) by 0 days.

(21) Appl. No.: 09/739,574

(22) Filed: Dec. 18, 2000

(51) Int. Cl.[7] .................................. A61N 1/04
(52) U.S. Cl. ................ 600/509; 600/341; 600/392; 600/393; 600/382; 607/152
(58) Field of Search .................. 607/142, 152; 600/391–393, 509, 382

(56) References Cited

U.S. PATENT DOCUMENTS

| | | | |
|---|---|---|---|
| 3,954,100 A | 5/1976 | Sem-Jacobsen | 128/2.06 E |
| 3,960,141 A * | 6/1976 | Bolduc | 128/2.06 E |
| 4,033,333 A * | 7/1977 | DeSalvo et al. | 128/2.06 E |
| 4,233,987 A | 11/1980 | Feingold | 128/639 |
| 4,354,509 A * | 10/1982 | Strahwald et al. | 128/803 |
| 4,583,549 A * | 4/1986 | Manoli | 128/640 |
| 5,184,620 A | 2/1993 | Cudahy et al. | 128/639 |
| 5,257,631 A | 11/1993 | Wilk | 128/710 |
| 5,327,888 A | 7/1994 | Imran | 128/640 |
| 5,445,149 A | 8/1995 | Rotolo et al. | 128/644 |
| 5,782,238 A | 7/1998 | Beitler | 128/639 |
| 5,951,598 A * | 9/1999 | Bishay et al. | 607/142 |
| 6,066,093 A * | 5/2000 | Kelly et al. | 600/386 |
| 6,117,077 A * | 9/2000 | Del Mar et al. | 600/301 |

\* cited by examiner

*Primary Examiner*—Carl Layno
(74) *Attorney, Agent, or Firm*—Leonard Bloom & Associates, LLC (57) ABSTRACT

Disclosed is an electrode placement with a series of electrodes disposed therein to be used for a one-step placement of electrodes. The device is shaped to allow it to be positioned and placed on a patient so that accurate placement of electrodes is achieved.

8 Claims, 6 Drawing Sheets

ELECTRODE PLACEMENT DEVICE FOR TAKING ELECTROCARDIOGRAMS AND METHOD OF USE

FIELD OF THE INVENTION

The present invention finds applicability in the field of electrocardiograms; and more specifically placing leads on a patient prior to taking an electrocardiogram.

BACKGROUND OF THE INVENTION

1. Background Information

Most 12-lead EKG requires specifically trained personnel to place nine separate electrodes that adhere to specific areas of the patient's body. A wire to a monitor connects each electrode. Electrical activity of the heart is transformed into a wave form via a computer and displayed on a screen or recorded on graph paper in 12 different views or "leads". The leads are various combinations of the electrodes. An alarm system signals when a lead is missing or malfunctioning.

The placement of leads in a 12-lead EKG is described in U.S. Pat. No. 5,184,620 to Cudahy, the contents of which are incorporated herein in their entirety. The leads show views of the heart in two planes. The frontal plane view uses different combinations of electrodes L1, L2 and L3 to create six different leads. The horizontal plane view uses each of the precordial electrodes V 1–6 to create six different leads. Together, there are a total of twelve leads. This describes the routine 12-lead EKG most commonly used.

A standard 12-lead electrocardiogram (EKG) provides a comprehensive picture of the heart's electrical activity. Each lead provides a different view.

The six limb leads originate from three electrodes placed on the patient's arms and left leg. The limb electrodes are marked with abbreviations: LL (left leg), RA (right arm), and LA (left arm). They provide the basis for the three standard limb leads and the three augmented limb leads.

The three standard limb leads (I, II, and III) represent the difference in bipolar electrical potential between two of the limb electrodes, as follows: (one electrode is positive, one is negative)

lead I: right arm (−)/left arm (+)
lead II: right arm (−)/left leg (+)
lead III: left arm (−)/left leg (+)

The three argmented limb leads (AVR, AVL and AVF) use the same three electrodes as the standard limb leads I, II and Im to measure the unipolar electrical potential in one electrode in reference to the other two electrodes:

lead AVR: right arm (+) in reference to left arm (−), left leg (+)
lead AVL: left arm (+) in reference to right arm and left leg
lead AVF: left leg (+) in reference to left arm and right arm.

For a horizontal view from the heart to an electrode placed on the chest, one looks to the six precordial leads ($V_1$ and through $V_6$). For an accurate lead recording on the ECG, one needs to place the chest electrodes correctly. One starts by finding the proper landmarks for $V_1$—fourth intercostal space, right sternal border-because this position will be your guide for placing the other chest electrodes.

To place the electrode for $V_1$, one follows these steps:

First, palpate the jugular notch (a depression).

Move inferiorly and palpate the solid manubrium.

Continue to move inferiorly and feel the angle of Louis (sternal angle), which is at the top of the sternal body.

Directly to the right of the angle of Louis is the second right rib. Below the second right rib is the second intercostal space.

Move your fingers down, palpating the next two ribs. Below the fourth rib and to the right of the sternal body is the fourth intercostal space. Place the $V_1$ electrode here.

Then place $V_2$ through $V_6$ as follows:

$V_2$: fourth intercostal space, left sternal border
$V_3$: midway between $V_2$ and $V_4$
$V_4$: fifth intercostal space, left midclavicular line
$V_5$: same level as $V_4$ at anterior axillary line
$V_6$: same level as $V_4$ at left midaxillary line.

The lead placement must be precise within a few centimeters, requiring knowledge and skill. The education and training of personnel is time consuming and expensive. The procedure may only be available where there are trained personnel. There is variability in placement between personnel and each new procedure, leading to variability in readings. The placement of each lead or electrode in the designated anatomical position often requires repeated attempts. This limits the use of the 12-lead EKG in emergency settings. Multiple pieces of equipment (electrodes, clips, wires, etc.) and connection sites carry the risk of damage, loss of improper use and the knowledge to detect and correct the problem. In addition, extra pieces of equipment must be available and functional in each setting used. The additional training and equipment add costs.

2. Prior Art Patents

Beitler (U.S. Pat. No. 5,782,238) discloses a flexible multiple electrode lead EKG device for patient-attachment. There are switches on the electrodes for activating the proper electrode. The device is weighted for attachment rather than through adhesion.

Wilk (U.S. Pat. No. 5,257,631) teaches an electrocardiographic device which is coextensive with the chest of the patient being tested. The device is weighted and attached by straps.

Cudahy (U.S. Pat. No. 5,184,620) teaches an electrode pad having a plurality of electrode sites. The electrode placement device is held in place by adhesive. The configuration of the Cudahy device does not allow for accurate placement of the device across the chest because of the lack of a visual guide relative to the body.

The following patents also show multiple electrode EKG devices for hooking a patient to an electrocardiograph instrument.

| | |
|---|---|
| Sem-Jacobsen | 3,954,100 |
| Imram | 5,327,888 |
| Rotolo | 5,445,149 |
| Feingold | 4,233,987 |

None of the prior art patents show the unique features of the electrode placement device as described by the herein disclosed invention.

SUMMARY OF THE INVENTION

The herein described invention is designed to facilitate electrode placement by eliminating single lead electrode placement habitually resorted to in the prior art.

The herein disclosed invention requires no special skill to use, thereby eliminating the cost of training personnel and eliminates the need for skilled personnel. This in turn allows the device to be used in a much wider variety of settings such as cardiac stress testing, operating rooms, radiological suites, in the field, ambulance, emergency rooms, catheterization laboratories, outlying facilities, doctors offices, geriatric centers, and other care provider settings. Variability in readings is largely minimized. There is a great decrease in time required to place the device, which allows for use in emergency settings. The number of parts and pieces of equipment are reduced and most are disposable. The design allows a cost savings as no material is wasted in construction of a triangle (e.g., a square or rectangle cut in half), as opposed to configurations currently in use. The choice of adapters (provided along with the device) allow the device to be universally used with almost any EKG machine. The device could be used as well with an electronic system which would allow for remote readings.

Described another way, the electrode placement device is to be used for taking an electrocardiogram and, preferably, has a triangular applicator to be applied to the chest of a patient prior to taking an electrocardiogram. The device is sized to fit the patient and the top portion of the device is straight across to ensure accurate placement of the device. The device is in the shape of a triangle and has electrodes placed therein. The device can be placed on the patient during an emergency situation and kept on that patient in the ambulance, in the emergency room, operating room and recovery room. The device can be described comprehensively as being a disposable electrode lead placement device intended to be applied by a doctor, nurse or technician to a patient's chest for the purpose of facilitating EKG readings on the patient's heart. One of the contacts or electrodes of the device is marked on the front portion of the device and clearly visible externally thereof, such that the doctor, nurse or technician may quickly position that one electrode at an approximately correct predetermined location on the patient's chest and then align the straight top edge of the device substantially in a horizontal plane, such that the remaining contacts in the array of prepositioned contacts on the device are thereby disposed in a substantially correct alignment with respect to respective locations in the patient's chest from which the EKG readings are to be taken. The disposable device has a plan outline which is substantially triangular and includes a right angle corner, and wherein a contact is disposed adjacent to the right angle corner.

The device is intended to be maintained on the patient's chest for a time interval from an initial emergency situation through treatment until recovery, such that a datum is established for the patient, and such that any deviation from that datum may be quickly observed.

The device can be used in a method of obtaining early EKG readings from a patient in an emergency situation and thereafter taking periodic EKG readings on the patient and readily detecting any significant differences in the EKG readings indicative of a particular problem being experienced by the patient during diagnosis, treatment and recovery. This method includes the steps of providing a disposable device in a sterile package, the package providing indicia and instructions externally thereon, such that an emergency medical technician may quickly position the device on the patient's chest in an approximately desired location. An adhesive is provided on the back portion of the device along with providing a peel-off protective layer for the device.

With the problems attendant to use of conventional electrodes, the herein disclosed invention has the following objectives:

- to provide a device which makes placement of EKG electrodes simple and accurate.
- to provide a relatively-inexpensive disposable device for use with an electrocardiogram (EKG) device which is inexpensive.
- to produce an electrode placement EKG device which is easy to use.
- to produce an electrode placement EKG device which requires no special training for use.
- to provide an electrode placement EKG device with universal applicability.
- to provide an electrode placement EKG which is "fail safe".

These and other objects of the present invention will become apparent from a reading of the specification taken in conjunction with the enclosed drawings.

DESCRIPTION

Figure 1:
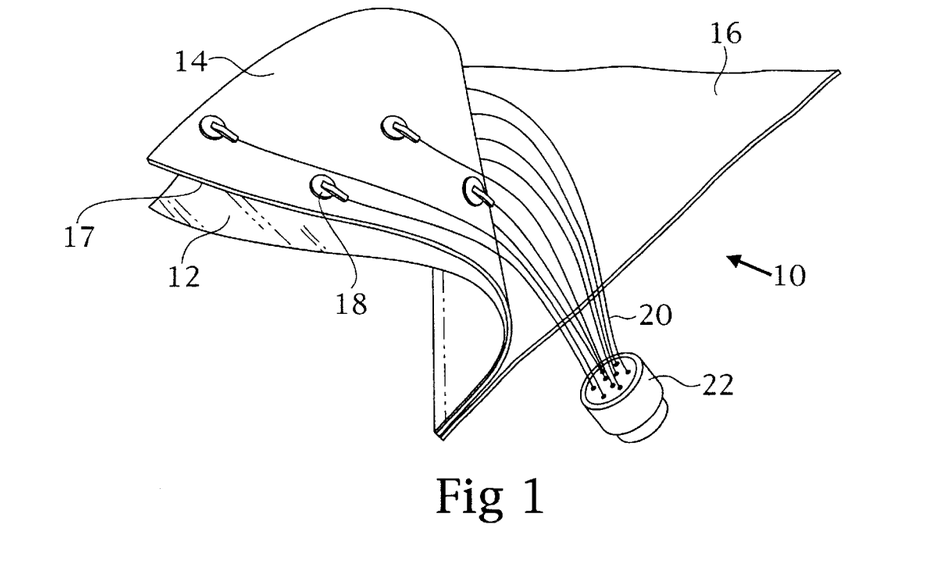
FIG. 1 is a perspective view of the electrode placement device of this invention.
Figure 2:
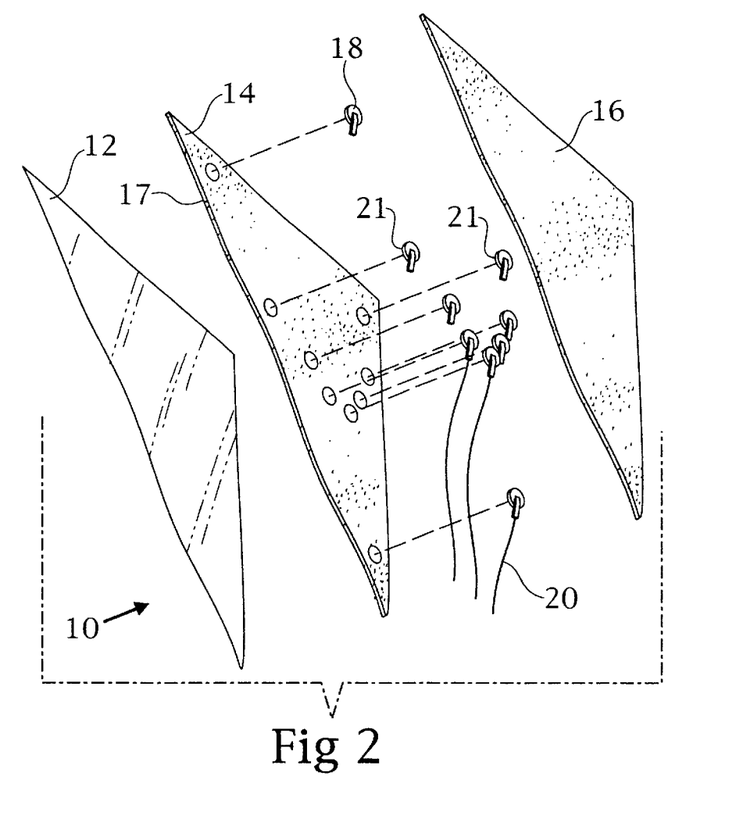
FIG. 2 is a disassembled (exploded perspective) view thereof.

Referring to FIGS. 1 and 2, the electrocardiogram (EKG) electrode placement device 10 has three layers (best shown in FIG. 2); a peel-off protective cover 12, an electrode containing layer 14 and the top surface cover 16. The contact surface 17 of the electrode containing layer 14 has a coating of adhesive 26 and at the electrode surface 19 there is a conductive coating 21. The adhesive coating 26 and the conductive coating 21 are best shown in FIGS. 3 and 4.

Figure 12:
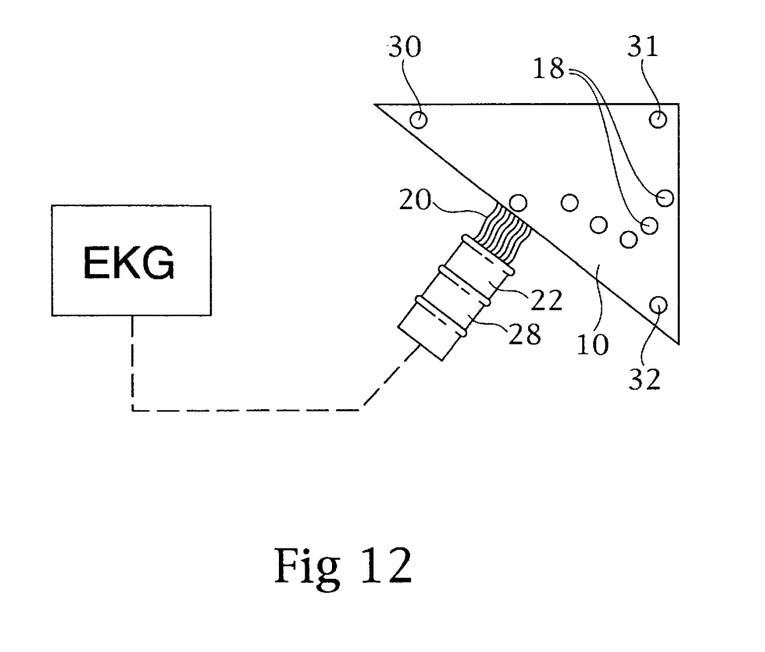
FIG. 12 is a view of the lead placement device attached to the EKG recording unit, using an adapter (if necessary).

Referring to FIG. 2, all of the electrodes (or contacts) 18 are attached to leads 20; however, for ease of illustration not all of the electrodes 18 are shown with leads. As best shown in FIG. 12, all of the leads 20 will be ganged together and fitted to a terminal connector 22. The electrode containing layer 14 has the adhesive coating 26 and a conductive coating 21 on the surface of the electrodes 18.

In a preferred embodiment, nine leads are employed in the device. The placement of leads to the electrodes is clearly set forth in FIG. 11.

Figure 3:
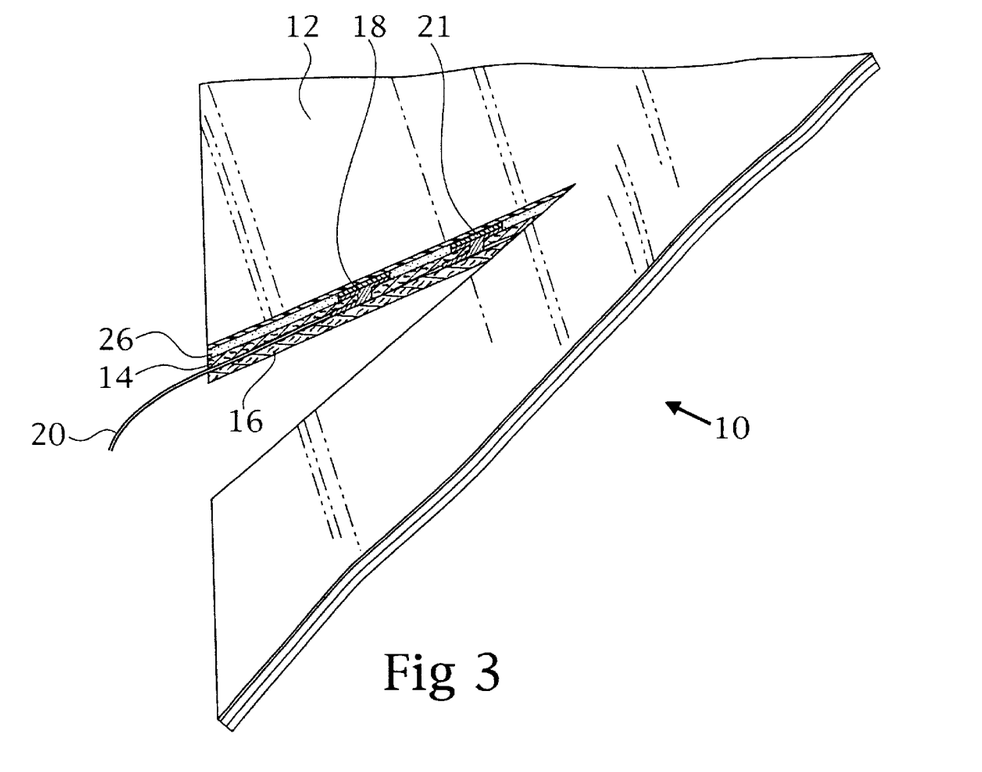
FIG. 3 is a perspective view thereof with part of the device cut-away to show its interior.
Figure 4:
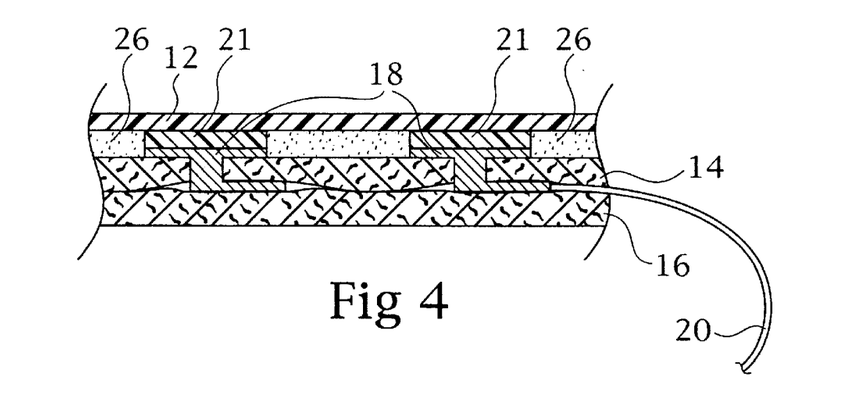
FIG. 4 is an enlarged sectional view of the interior of the device as viewed from the cut-away of FIG. 3.

With reference to FIGS. 3 and 4, the placement of electrodes 18 within the device is illustrated. Each electrode 18 is attached to a lead 20 which in turn is attached to a terminal 22 (best shown in FIG. 11). In actuality, the device can be conceptualized as having four layers, namely, the protective cover 12, the adhesive layer 26, the electrode retaining layer 14, and the top surface cover 16. A conductive layer 21 covers the electrode surface.

Figure 5:
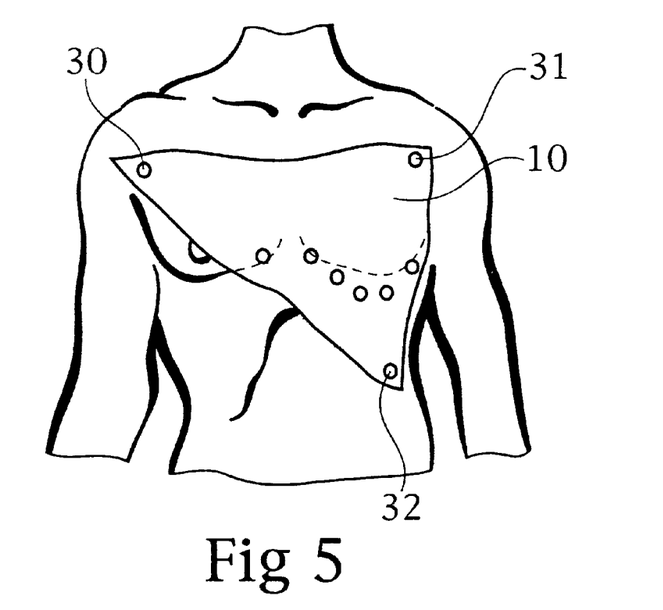
FIG. 5 is a view showing the electrode placement device applied to the chest of a male patient.
Figure 6:
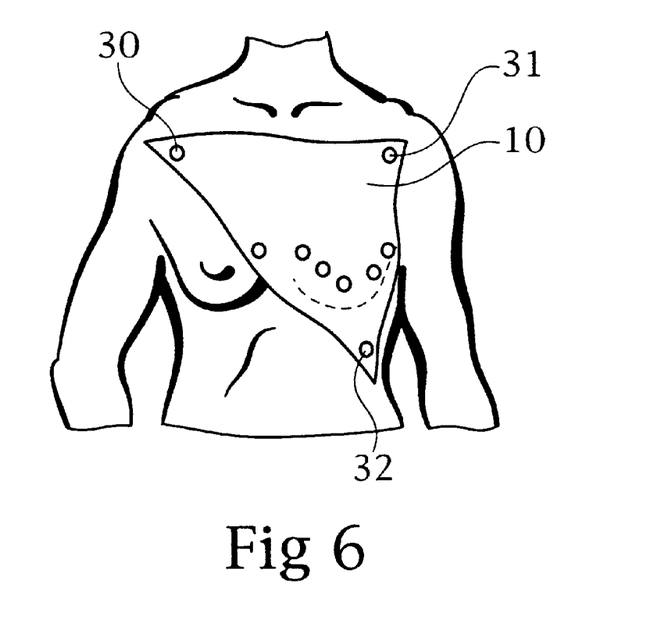
FIG. 6 is a view showing the electrode placement device applied to the chest of a female patient.

FIGS. 5 and 6 are views illustrating the position of the electrode placement device on the male chest (FIG. 5) and the female chest (FIG. 6).

Figure 7:
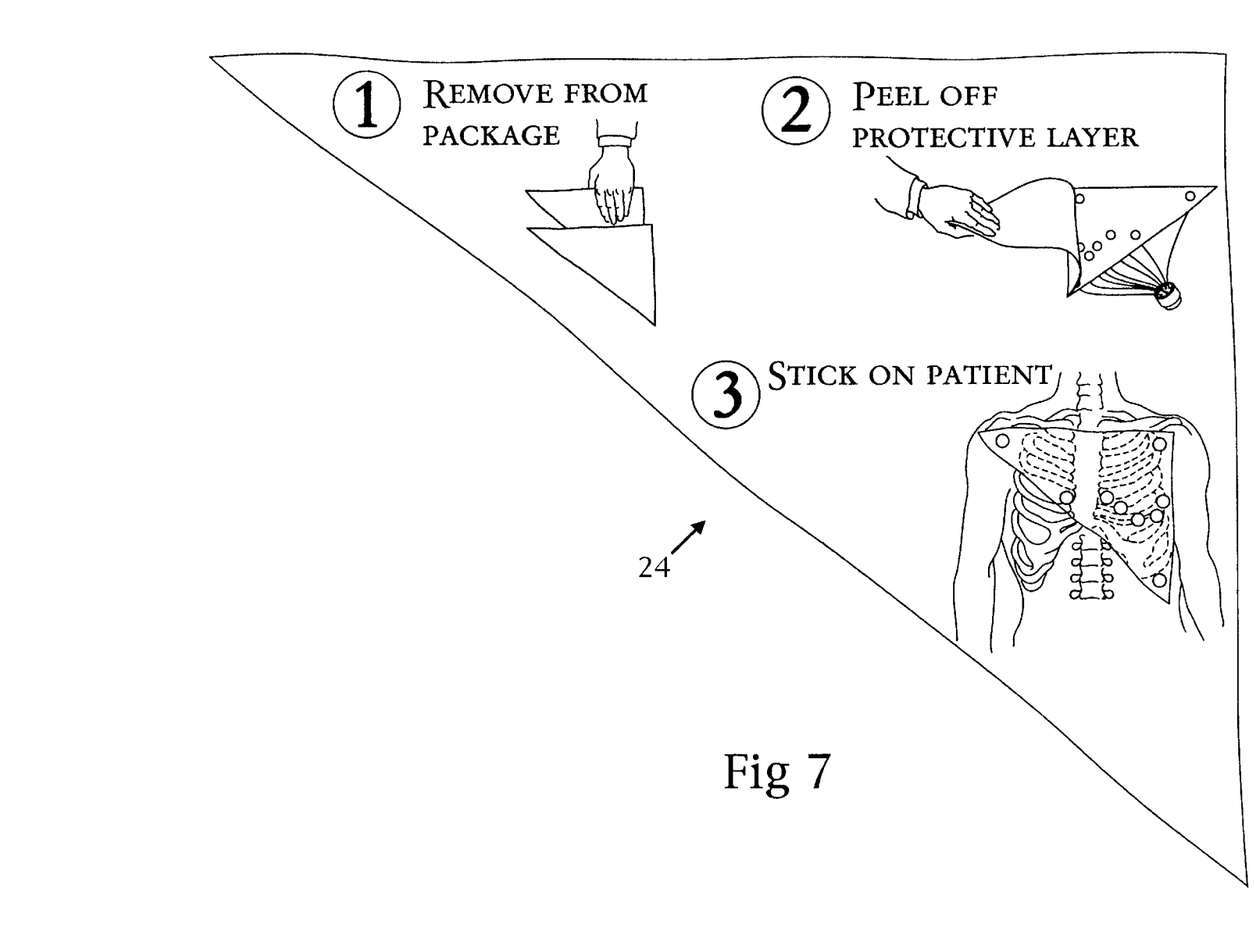
FIG. 7 is a view of the packet (sterile package) in which the EKG electrode placement device is supplied.

FIG. 7 is a view of the external surface of the packet 24 with instructions for use. The EKG electrode placement device 10 is shown fitted to the patient prior to being removed for use. This simplifies use for all users of the device.

Figure 8:
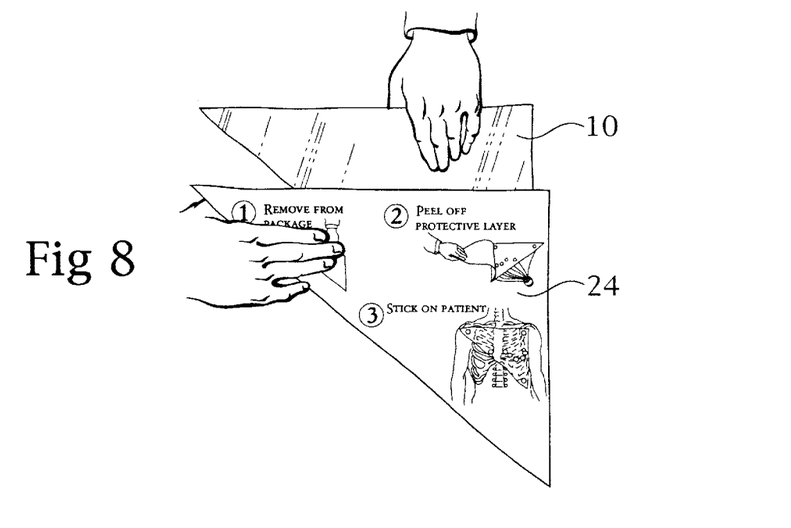
FIG. 8 is a view of removing the electrode placement device from the packet.
Figure 9:
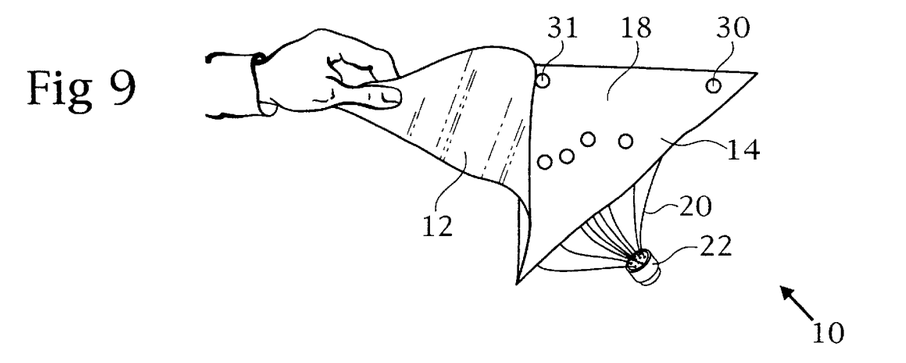
FIG. 9 is a view showing the protective peel-off cover being removed from the adhesive layer of the electrode placement device.
Figure 10:
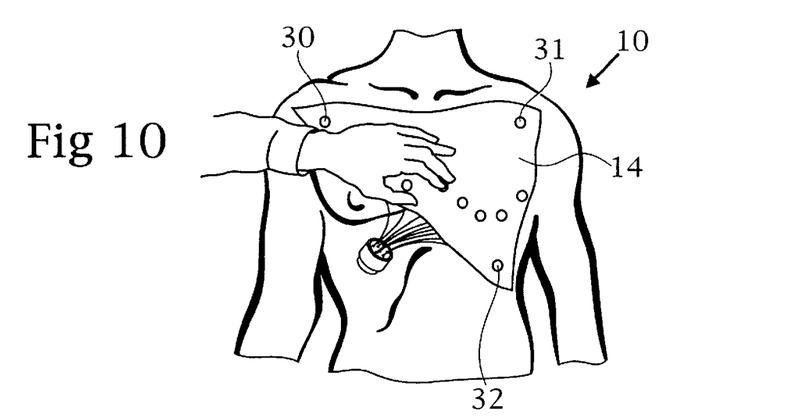
FIG. 10 is a view showing the lead placement device over the chest of a patient.

FIGS. 8 to 10 show the steps to be taken for applying the electrode placement device 10: removing the device from packet 24 (FIG. 8); removing the protective peel-off cover 12 from the adhesive layer (FIG. 9); and placing the device on the chest of patient (FIG. 10). The electrode placement device 10 is applied by first applying the right arm point 30 to the chest, then the left arm point 31 to the chest and then pressing the top surface cover 16 and electrodes 18 to the chest. This will adhere the electrodes 18 in their proper place for EKG reading. Once the electrode placement device 10 is applied to the chest, the terminal connector 22 is attached to the connector 28 of the EKG unit (FIG. 12). Readings can then begin.

Figure 11:
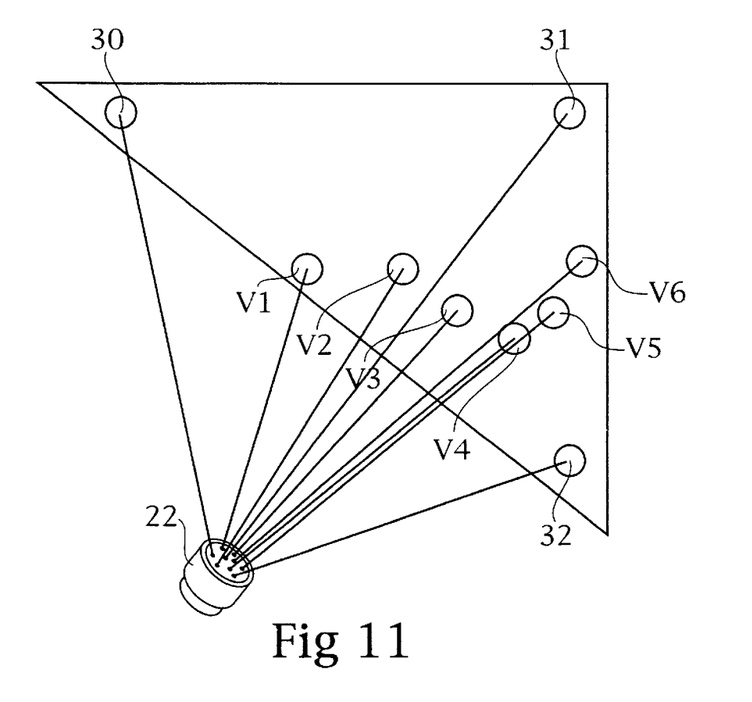
FIG. 11 is a view of the electrode positions of a 9-lead electrode positioning device. The leads are placed on positions V1–V6, and at the three corners of the triangle.

With reference to FIG. 11, the relative positions of the electrodes as applied to the chest are shown. These are conventional placement points. The device has nine electrodes 18; however, the device 10 could be fashioned to have twelve or more electrodes.

Technically speaking, the technician applying the device would use the right and left outer borders of the clavicles, where they meet the shoulders as the upper border of the device and the lower left corner should lie within the last three ribs on the anterior axillary line, with the left border being perpendicular to the upper border.

The preferred device of this invention is in the shape of an isosceles or equilateral triangle. The sensing units or electrodes 18 of the "multi-electrode device" 10 of this invention are embedded between two triangle-shaped pieces of material in correct anatomical positions for electrode placement. The triangles and sensing electrodes units are made from materials commonly used and described below, under "options". The underside of the device, which will be in contact with the skin, will allow a small exposed area of each sensing unit to come into direct contact with the skin. There will be a type of gel commonly used and described below to enhance conductivity between the skin and sensing unit. There will be a type of adhesive on the underside of the device that is in contact with the skin made from a commonly used material described below. Each sensing unit or electrode will be permanently attached to a wire, and the wires will exit the triangle "multi-electrode" either bound in a single cable or separate. The inventor conceptualizes the electrode placement device of this invention to be disposable. There will be a combination of connectors and cables that will allow for universal connections to most monitors and electrocardiogram machines. The package containing the device as well as the device itself will have illustrations to show exactly where to place the device on the patient.

In using the electrode placement device of this invention, a triangle is preferred because of the cost savings in the material. An isosceles or equilateral triangle is not mandatory; any triangle will do.

The sizes will be "S, M, L" (small, medium, large). The diagram of the body will be printed on the front of the device (also on the package) so that use of the product will be easy to use by the most inexperienced technician.

In an emergency, the Emergency Medical Technicians (EMT's) are eager to get the patient to the Emergency Room (ER). They don't take the time, presently, to apply the "buttons" or suction cups for an Electrocardiogram (EKG). It takes too long and requires training and skill. They have to get the patient to the ER quickly. The herein disclosed invention remedies this problem, and the device is easy to use and can be used in emergency situations.

The leads of the inventive device are sandwiched between the two layers of material. The material is soft and flexible. A cover sheet (on the back) is lifted off by the nurse or "tech" to expose the adhesive and electrodes, and the device is positioned on the patient's chest. The adhesive is in contact with the patient's skin. It is just like the adhesive used on the present disposable "buttons".

The individual leads can be surrounded by perforations so that they can be moved for more accurate placement.

The device will interface via an adapter with any EKG machine. There are four or five standard machines. The short wires coming off of the device will be bundled into a connector and, through an adapter 28, to the EKG. Or the connector may be fitted to a particular EKG.

The preferred number of electrodes used in the device of this invention is nine, however, more or fewer electrodes could be used.

In using the device, it is only necessary for the device to be fitted in a proximate position. (Of course, the more precise, the better.) The important thing is to be consistent, to establish a database for future readings with that particular patient. The device stays in place. There are no leads or ("buttons") to be moved around. It's the differences (from previous readings) which are important.

If not positioned right, peel it off and re-position it. Or toss it away and use another one.

For adults, male or female, the device would be sized accordingly:
S=90–140 pounds
M=140–180 pounds
L=180+pounds For children we would need around 4 or 5 different sizes.

Sizes for male and female don't vary too much, except for large breasted females.

The "buttons" on the leads could be in a perforated area which could be popped out to reposition a particular "button" if necessary.

By convention there are now 12 leads being used. But in the field, around three are applied.

With 12 leads, you would get much more information on the condition of the patient's heart. The inventive device is described with nine leads but could be fashioned to contain more leads.

The herein described invention contemplates a comprehensive method of use. This is possible since the electrode placement device can remain in place from the time that the emergency medical technician places the device on the patient (1) during an emergency, (2) in the ambulance, (3) in the emergency room, (4) in the operating room, (5) in the intensive care unit and in the (6) recovery room. This is a major advantage since the EKG readings will be consistent.

Variability of readings due to placing and replacing electrodes will be eliminated.

In a preferred embodiment of the present invention, the electrodes (contacts or sensing elements) 18 may be chlorodized silver or copper/nickel alloys. The conducting gel may be hypoallergenic, solid or wet. The material for the "triangles" may be foam latex free, fabric (+/−non-woven, +/−stretchable), and hypoallergenic, ventilated, vinyl tape, fluid resistant. The adhesive is diaphoretic and high "tack". Other variations or options comprise perforations around the sensing unit in various shapes and sizes, allowing them to stay adhered to the patient while the extra adhesive material is removed (for prolonged use of the electrodes), color coding in various ways, alternative for use on the back instead of the chest, various adult and pediatric sizes, adaptations to allow for veterinary use, pull-tabs, lead or cable lock design, and/or x-ray translucent materials.

It will be appreciated by those skilled in the art that many advantages accrue from the use of the electrode placement device of the present invention, as follows:

1) The device is disposable. This eliminates a potential source of patient-to-patient infection.
2) The device is relatively inexpensive.
3) The device follows the standard lead pattern which is built in. Although this feature is not necessarily critical, variations of configuration of electrodes is possible.
4) The device has a universal adaptor which can be used anywhere in the world.
5) The device comes in a package with easy to use instructions and a placement diagram.
6) No special skill or training is required to use the device.
7) The device is faster and easier to use than conventional devices.
8) Using the device of this invention eliminates variability in placement and replacement.
9) The triangular configuration uses less material (from a cost standpoint).
10) The device of this invention is easy to use in emergency medical situations.
11) The device can be kept in place even with the patient going into the emergency room or operating room.
12) The device could also be used for regular periodic exams as well as for stress tests.
13) The device is sized to fit the patient.
14) The device can be used in the field as well as the office.

Obviously, many modifications may be made without departing from the basic spirit of the present invention. Accordingly, it will be appreciated by those skilled in the art that within the scope of the appended claims, the invention may be practiced other than has been specifically described herein.

I claim:

1. A disposable electrode lead placement device intended to be applied by a doctor, nurse or technician to a patient's chest for the purpose of facilitating EKG readings on the patient's heart, the device comprising respective front and back portions and a substantially straight top edge and having an array of pre-positioned electrodes extending from the back portion of the device, a lead carried by each of the electrodes, the leads extending externally of the device and being carried by a terminal connector intended to be connected to the EKG, the position of at least one of the electrodes being marked on the front portion of the device and thereby clearly visible externally thereof, such that the doctor, nurse or technician may quickly position the one electrode at an approximately correct predetermined location on the patient's chest and then align the straight top edge of the device substantially in a horizontal plane, such that the remaining electrodes in the array of prepositioned electrodes on the device are thereby disposed in a substantially correct alignment with respect to respective locations in the patient's chest from which the EKG readings are to be taken, and means for removably securing the device to the patient's chest.

2. The disposable device of claim 1, wherein the device has a plan outline which is substantially triangular and includes a right angle corner, and wherein the said one electrode is disposed adjacent to the right angle corner.

3. The disposable device of claim 2, wherein the triangular plan outline of the device has two additional corners, each of which has an electrode disposed adjacent thereto.

4. The disposable device of claim 1, wherein the means for removably securing the leads to the patient's chest comprises an adhesive on the back portion of the device.

5. The disposable device of claim 4, further including a peel-off protective layer for the adhesive on the back portion of the device.

6. The disposable device of claim 1, wherein the leads are sandwiched between the front and back portions of the device.

7. The disposable device of claim 1, further including an adapter between the connector and the EKG, thereby making the device universal for various EKGs.

8. The disposable device of claim 1, wherein the device is intended to be maintained on the patient's chest for a time interval from an initial emergency situation through treatment until recovery, such that a datum is established for the patient, and such that any deviation from that datum may be quickly observed.

* * * * *